United States Patent [19]

North et al.

[11] Patent Number: 5,693,591

[45] Date of Patent: Dec. 2, 1997

[54] ACTIVITY PROMOTING ADDITIVES FOR REST-BREAKING AGENTS

[75] Inventors: Michael Shaun North, Arnhem; Robert Jan Butselaar, Hilversum, both of Netherlands

[73] Assignee: Akzo Nobel N.V., Arnhem, Netherlands

[21] Appl. No.: 535,280

[22] PCT Filed: Apr. 14, 1994

[86] PCT No.: PCT/EP94/01180

§ 371 Date: Dec. 27, 1995

§ 102(e) Date: Dec. 27, 1995

[87] PCT Pub. No.: WO94/23574

PCT Pub. Date: Oct. 27, 1994

[30] Foreign Application Priority Data

Apr. 20, 1993 [EP] European Pat. Off. ............. 93201138

[51] Int. Cl.$^6$ .................. A01N 25/30; A01N 33/22; A01N 59/24
[52] U.S. Cl. ............. 504/116; 504/188; 504/354
[58] Field of Search ................... 504/116, 188, 504/354

[56] References Cited

U.S. PATENT DOCUMENTS

| | | | |
|---|---|---|---|
| 4,525,200 | 6/1985 | Kimpara et al. | 71/76 |
| 4,556,410 | 12/1985 | Ronning et al. | 71/78 |
| 4,936,899 | 6/1990 | Schulz et al. | 71/73 |

FOREIGN PATENT DOCUMENTS

| | | | |
|---|---|---|---|
| 0 232 755 | 8/1987 | European Pat. Off. | A01N 45/00 |
| 0 257 686 | 3/1988 | European Pat. Off. | A01N 25/30 |
| 0 347 988 | 12/1989 | European Pat. Off. | C11D 3/39 |
| 0 463 241 A1 | 2/1992 | European Pat. Off. | A01N 33/08 |
| 1 604 321 | 12/1981 | United Kingdom | C05C 1/00 |
| 2 257 044 | 1/1993 | United Kingdom | A01N 25/00 |

OTHER PUBLICATIONS

*Artificial Rest–Breaking of Apricot and Plum Cultivars using Hydrogen Cyanamide*, J.D. Stadler, M.S. North and G.F.A. Lotze, Fruit and Fruit Technology Research Institute, J.S. Afr. Soc. Hort. Sci. 1.(1) May 1991.

Abstract of EP 0 272 542 A2 (BASF) Jun. 1988.

Improved Methods for Breaking Rest in the Peach and Other Deciduous Fruit Species. *J. Amer. Soc Hort Sci.* 96(4):519–522, 1971.

Effect of cyanamide and DNOC/oil on budbreak, yield and fruit size Golden Delicious apples. *S–Afr. Tydskr, Plant Grond* 1989 6(3).

Overcoming rest at different growth stages with hydrogen cyanamide *Scientia Horticulturae*, 50 (1992) 107–113.

Alternative rest–breaking agents to DNOC/oil for apples *S. Afr J. Plant Soil* 1992 9(1).

Effects of autumnal nitrogen nutrition, urea sprays and a winter rest–breaking spray on budbreak and blossoming of young Golden Delicious trees grown in sand culture. *The Deciduous Fruit Grower* Jan. 1973.

Dormancy Release in Deciduous Fruit Trees. *Horticultural Reviews* vol. 7, pp. 239–300, AVI Publishing Co. Westport,, CT (1985).

Time of Thiourea–KNO$_3$ Application on the Rest Requirement and Bud Development in Loring Peach[1] *HortScience* 11(4): 400–402. 1976.

Chemical treatments for breaking rest in peach in relation to accumulated chilling. *Journal of Horticultural Science* (62) 4(1987) 457–461.

*Derwent Publications Ltd.* 43–700–192/27 SKW Trostberg AG Jun. 1983.

Chemical Dormancy Breaking of Red Rasberry. *Hort Science* 18(5):710–713. 1983.

Coggins, C. W. et al. "Possible methods to increase efficacy of gibberellic acid applied to navel orange trees", Chapter 55 of *Adjuvants for Agrichemicals*. Chester L. Foy, Ed. CRC Pr. P. 567–572. 1992.

*Primary Examiner*—S. Mark Clardy
*Attorney, Agent, or Firm*—Ralph J. Mancini; Louis A. Morris

[57] ABSTRACT

Activity promoting additives (alkoxylated amines and alkoxylated quaternary ammonium compounds) for rest-breaking agents are disclosed. Further, rest-breaking compositions comprising these additives and a rest-breaking agent are also disclosed. Finally, a process for breaking the rest of deciduous fruit trees is disclosed. The activity promoting additives enhance the activity of rest-breaking agents thereby leading to improvements in the yields and quality of fruit from deciduous fruit trees in regions which have mild winter weather conditions.

11 Claims, No Drawings

5,693,591

ACTIVITY PROMOTING ADDITIVES FOR REST-BREAKING AGENTS

This application has been filed under 35 USC 371 as a national stage application of PCT/EP94/01180, filed Apr. 14, 1994.

The present invention relates to the use of particular compounds as activity promoting additives for rest-breaking agents, to rest-breaking compositions comprising these additives and to the use of these compositions for rest-breaking of deciduous fruit trees.

BACKGROUND OF THE INVENTION

Deciduous fruit trees require winter chilling to grow normally. The amount of chilling required depends upon the kind of fruit and the cultivar. If winter chilling is insufficient, then growth abnormalities such as delayed and uneven blossoming, poor leaf cover, insufficient fruit-set and reduced fruit size can occur. These symptoms are generally referred to as delayed foliation according to the article, Blommaert, K. L. J., "Winter Dormancy and Delayed Foliation," *The Deciduous Fruit Grower*, (1956).

Measures to reduce the symptoms of delayed foliation include treatment with high volumes of chemical rest-breaking agents during later winter and various physical manipulations such as pruning.

In South Africa, for example, most apple trees receive insufficient winter chilling to break rest completely and thus annual application of a chemical rest-breaking agent is standard practice. The most widely used rest-breaking agent in commercial apple orchards is dinitro-ortho-cresol (DNOC) in combination with winter-oil emulsion (a lipophilic agent) (Erez, A. et al., "Improved Methods of Breaking Rest in the Peach and Other Deciduous Fruit Species," *J. Amer. Soc. Hort. Sci.*, 96, pp. 519–522 (1971)). This article also mentions the use of the potassium salt of gibberellic acid, kinetin, indoleacetic acid and thiourea as potential rest-breaking agents. DNOC is a non-systemic stomach poison and contact insecticide, ovicidal to the eggs of certain insects. It is strongly phytotoxic and its permissable use as an insecticide is limited to dormant sprays or on waste ground. Further, DNOC is known to act as a cumulative poison in man. Although DNOC is relatively inexpensive and effective as a rest-breaking agent, it is toxic enough to limit its continued use and it is currently on the European Red List of agricultural chemicals which will be prohibited in the future. DNOC is also banned in the United States for use as an agricultural chemical.

One of the most effective alternatives to DNOC is hydrogen cyanamide according to the publications, Snir, I., "Chemical Dormancy Breaking of Red Raspberry," *HortScience*, 18, pp. 719–713 (1983); North, M. S., "Effects of Cyanamide and DNOC/oil on Budbreak, Yield and Fruit Size of Golden Delicious Apples," *S. Afr. J. Plant Soil*, 6(3), pp. 176–178 (1989); Stadler, J. D., North, M. S. and Lutze, G. F. A., "Artificial Rest-Breaking of Apricot and Plum Cultivars Using Hydrogen Cyanamide," *J.S.Afr.Soc.Hort.Sci.*, 1(1), pp. 9–11, (1991); Nee, C. C. and Fuchigami, L. H., "Overcoming Rest at Different Growth with Hydrogen Cyanimide," *Scientia Horticulturae*, 50, pp. 107–113 (1992); and North, M. S., "Alternative Rest-Breaking Agents to DNOC/oil for Apples," *S. Afr. J. Plant Soil*, 9(1), pp. 39–40 (1992).

Hydrogen cyanamide is a skin and eye irritant and is especially acute when used in combination with the consumption of alcohol. The toxicity and relatively high price limit its market acceptance and hydrogen cyanamide has also been placed on the European Red List.

Thus, there exists an immediate need for new, milder rest-breaking agents, not only in South Africa, but also in countries which are currently developing deciduous fruit industries but do not have an ideal climate therefor, such as Brazil. Further, there is a need for such new rest-breaking agents in countries with existing deciduous fruit industries that, up to now, did not appreciate the extent of the problem of delayed foliation.

The response of a tree to a rest-breaking agent is dependent upon the chemical composition of the agent, its application rate and timing and on the nutritional status of the tree according to Terblanche, J. H. and Strydom, D. K., "Effects of Autumnal Nitrogen Nutrition, Urea Sprays and a Winter Rest-Breaking Spray on Budbreak and Blossoming of Young 'Golden Delicious" Trees Grown in Sand Culture," *Deciduous Fruit Grower*, 23 pp. 8–14 (1973).

Many chemicals have been found to have rest-breaking ability. A summary of some of these chemicals can be found in Saure, M. C., "Dormancy Release in Deciduous Fruit Trees," Janick, J. (Ed.), *Horticultural Reviews*, 7, pp. 239–287, AVI Publishing Co. Inc., Westport, Conn. (1985). The efficacy of these various rest-breaking agents appears to be directly related to their physiological harshness.

One of the milder rest-breaking agents is potassium nitrate which has been shown to have a positive effect on peaches. Generally, fruit trees having a lower chill requirement, such as peaches, also require lower concentrations of rest-breaking agents, whereas fruits with a higher chill requirement, such as apples, require excessive concentrations of a mild rest-breaking agent. Articles demonstrating the effects of thiourea, potassium nitrate and combinations thereof include, Wolak, R. J. and Couvilton, G. A., "Time of Thiourea-$KNO_3$ Application on the Rest Requirement and Bud Development in 'Loring' Peach," *HortScience*, 11(4), pp. 400–402, (1976) and Fernandez-Escobar, R. and Martin, R., "Chemical Treatments for Breaking Rest in Peach in Relation to Accumulated Chilling," *J. Hort. Sci.*, 62(4), pp. 457–461, (1987). EP-A-232755 discloses compositions comprising a gibberellin-type plant hormone which is known to have rest breaking activity, and a quaternary ammonium compound. The latter compound is a chlorine derivative which increases synergistically the activity of the gibberellin-type plant hormone.

DE-A-3150404 discloses compositions for breaking the dormancy in cultivated plants, in particular fruit trees, which contain hydrogen cyanamide (0.1–10%) and preferably also a wetting agent. The wetting agent which is used to promote absorption of the cyanamide into the plant, is an alkylaryl polyglycol ether type surfactant.

For the foregoing reasons, there exists a need in the art for improved rest-breaking agents which are, affordable, effective, less toxic than the present rest-breaking agents and which can be employed in reasonable concentrations.

SUMMARY OF THE INVENTION

The present invention relates to a process for breaking the rest in deciduous fruit trees which comprises the step of applying to at least one deciduous fruit tree before blossom, an effective amount of at least one rest-breaking agent and a compound selected from the group consisting of alkoxylated amines represented by the following general formula:

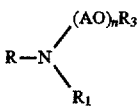

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

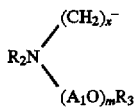

wherein m is an integer from 1–50, $A_1$ represents an alkylene group and when n>1, each $A_1$ may be the same or different alkylene groups, x is an integer from 1–6, and $R_2$ is independently selected from the same groups as R, $R_3$ is selected from hydrogen, 1–8 carbon atom straight or branched chain alkyl and alkenyl groups and aryl groups having up to 8 carbon atoms; and $R_1$ is selected from hydrogen, straight or branched chain alkyl and alkenyl groups having 1–22 carbon atoms, a group represented by the formula:

wherein n' is an integer from 1 to 50 and $A_2$ represents an alkylene group and when n'>1 each $A_2$ may be the same or different alkylene groups; and alkoxylated quaternary ammonium compounds represented by the following general formula:

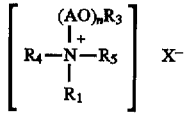

wherein n, A, $R_1$ and $R_3$ are as defined above, X is an anion, $R_5$ is selected from hydrogen, straight or branched chain alkyl or alkenyl groups having 1 to 4 carbon atoms and benzyl; or $R_5X$ can be carboxymethyl as in betaines and oxygen as in amine oxides; $R_4$ is selected from straight or branched chain alkyl and alkenyl groups having 8–22 carbon atoms and groups represented by the formula:

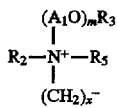

wherein $A_1$, m, $R_2$, $R_3$, $R_4$, $R_5$ and x are as defined above; to enhance the rest-breaking of the fruit tree.

More particularly, X may be halides such as $Cl^-$, $Br^-$, $CH_3SO_4^-$, and $C_2H_5SO_4^-$, among others. The anion associated with these quaternary ammonium compounds is not critical to the process of the present invention.

These compounds are known from European patent application publication number 0 463 241 where it is disclosed that these compounds are useful as blossom thinning agents for stone fruits. In addition, a small group of the foregoing compounds are known from European patent 0 257 686 which discloses several alkoxylated amines and their use as activity promoting additives for herbicides and fungicides. Also disclosed therein is a method for making these compounds, which method is hereby incorporated by reference.

As a result of extensive research it has now been found that the 5 above-identified compounds can be used as adjuvants for chemical rest-breaking agents for deciduous fruits. These compounds exhibit a substantial effect when combined with rest-breaking agents, and human toxicity and phytotoxicity studies have shown that these compounds have acceptably low levels of toxicity to humans and other plants. Further, the compounds do not cause significant harm to useful insect populations. Finally, the activity-enhancing effect of these compounds allows the use of milder rest-breaking agents which are less toxic, as well as the use of lower concentrations of rest-breaking agents.

The amino compounds of the present invention may be prepared by reacting an amine selected from the group consisting of R—$NH_2$, RRNH, and R—NH—$((CH_2)_x$—$NH)_n$—R' wherein R and R' are aliphatic hydrocarbon groups having 8–22 carbon atoms, n=1–5 and x is an integer from 1–6; with at least one alkylene oxide.

The preferred alkylene oxides for use in the present invention are ethylene oxide, propylene oxide, isobutylene oxide and butylene oxide. The compounds of the present invention are made in such a way as to introduce varying numbers of alkylene oxide units onto the amino nitrogen. Thus, these alkylene oxide groups may be all the same, such as, for example, one or more ethylene oxide units, or the groups may be different to form, for example, block copolymer chains of ethylene oxide and propylene oxide units, random copolymer chains consisting of several units of each of two or more different alkylene oxides, or alternating units of two or more alkylene oxides. Any conceivable combination of alkylene oxide units up to 50 units long may be employed at each location on the amino nitrogen which is to contain such units. In addition, a single amino nitrogen may contain two different alkylene oxide chains attached thereto or two chains which are the same.

In the most preferred embodiments of the present invention, block copolymer chains of ethylene oxide and one or more of propylene oxide or butylene oxide are employed. Preferably, the molar weight of the compounds used in the present invention is less than 8000 though higher molecular weight compounds can be employed in some circumstances.

The amino compounds can also be quaternized by known quaternization methods to produce quaternary ammonium compounds which are also useful in the process of the present invention. The fourth substituent added to the amino nitrogen by quaternization may be an alkyl, aryl or alkenyl group having 1 to 4 carbon atoms. The anion associated with such quaternary ammonium compounds is not critical to the process of the present invention.

Typical compounds suitable for use in the process of the present invention include, but are not limited to, cocobis (2-hydroxyethyl)methylammonium chloride, polyoxyethylene (15) cocomethylammonium chloride, oleylbis (2-hydroxyethyl)methylammonium chloride, polyoxyethylene (15) stearylmethylammonium chloride, cocobis (2-hydroxyethyl)amine, polyoxyethylene(5)cocoamine, polyoxyethylene(15)cocoamine, tallowbis (2-hydroxyethyl) amine, polyoxyethylene(5)tallowamine, polyoxyethylene (15)tallowamine, tallow/oleylbis(2-hydroxyethyl)amine, oleylbis(2-hydroxyethyl)amine, polyoxyethylene(5) oleylamine, polyoxyethylene(15)oleylamine, hydrogenated tallowbis(2-hydroxyethyl)amine, hydrogenated polyoxyethylene(5)tallowamine, hydrogenated polyoxyethylene(15)tallowamine, hydrogenated polyoxygthylene(50)tallowamine, N,N',N'-tris(2-hydroxyethyl)-N-tallow-1,3-diaminopropane, N,N',N'-polyoxyethylene(10)-N-tallow-1,3-diaminopropane, and N,N',N'-polyoxyethylene(15)-N-tallow-1,3-diaminopropane.

The process of the present invention is useful for rest-breaking of deciduous fruit to produce improvements advancing the time of bloom, budbreak and/or leaf cover and fruit set. The present process also enables the use of either milder rest-breaking agents or smaller quantities of harsher rest-breaking agents thus providing considerable advantages in toxicity to man and insect populations as well as safety advantages in the application of these agents.

When reference is made in this patent application to enhancement of rest-breaking, what is meant is that the time of bloom is advanced or one or more budbreak and/or leaf cover or fruit set are improved over a control tree.

The process of the present invention is to be applied to deciduous fruit trees prior to blossom. The process is particularly useful in growing areas where the winter chilling of the fruit trees is insufficient to provide good budbreak and fruit set for the particular fruit or cultivar. Winter chilling can be measured and is often represented by the unit, "Richardson Chill Units."

The optimum time to break rest for a particular deciduous fruit tree will depend upon several factors including the type of fruit, the cultivar, the climatic conditions and the type and amount of rest-breaking agent being applied. For some fruit or cultivar species, the best rest-breaking effects are accomplished by early application of the rest-breaking agent to the trees whereas for others it is best to wait until just before blossom. In general, the rest-breaking agent will be applied at some point between the time when winter has peaked and the time when blossoming begins.

One of the effects of the rest-breaking agents of the present invention is to accelerate the blossoming of the fruit trees. Accordingly, in the application of these rest-breaking agents consideration should be given to this effect and the agents should not be applied too early such that blooming occurs when there is still a risk of harsh weather.

The process of the present invention is carried out by the application of an effective amount of at least one rest-breaking agent in combination with an amount at least one compound as defined herein to enhance the rest-breaking activity of said rest-breaking agent. The rest-breaking compositions are preferably applied in the form of an aqueous solution in a concentration of 0.25 to 30% and more preferably from 0.5 to 10%. The lower limit is generally determined by the upper limit on application volume for the particular application equipment being employed, as well as by the type of fruit, the cultivar and the particular rest-breaking composition.

The upper concentration limit will generally be dictated by phytotoxicity considerations as higher concentrations of certain compounds have a localized phytotoxic effect on the trees. Thus, a concentration should be selected which provides adequate rest-breaking without unwanted phytotoxic effects on the remainder of the tree. The attached examples show that such concentrations can be selected by routine experimentation with the particular species of deciduous fruit.

The activity promoting additive of the present invention is generally employed in a concentration of 0.1–10.0% in the aqueous solution and more preferably, 0.2–5.0%. Again, the amount of activity promoting additive required will depend on the fruit, the cultivar and the particular rest-breaking agent, as well as the quantity of rest-breaking agent to be employed. Generally, the less rest-breaking agent employed, the more activity-promoting additive required to maintain the desired level of rest-breaking activity.

Rest-breaking agents which may be used in the process and composition of the invention include any known rest-breaking agent. Examples include hydrogen cyanamide, potassium nitrate, the potassium salt of gibberellic acid, kinetin, indoleacetic acid, thiourea and combinations thereof. The most preferred rest-breaking agent for use in the present invention is potassium nitrate.

The composition is preferably applied in a manner similar to the manner in which commercial insecticides are applied. More particularly, conventional equipment such as knapsack sprayers, hand held spray guns, mist blowers, and aerial spraying equipment among others may be used. The composition is applied the same way as in pesticide application.

The process of the present invention has the significant advantages that it breaks rest to the extent that the use of known, highly toxic rest-breaking agents can be eliminated or considerably reduced, it can be done in a manner which is safe for the crops and the treatment has no long term phytotoxic effect on the orchards, if carried out correctly. Further, the rest-breaking process will cause significantly less harm to beneficial insects when applied within the normal application volume, and the process appears to be environmentally acceptable, non-hazardous to operators of the application equipment, and non-corrosive to the equipment.

The present invention will be further illustrated by the examples appended hereto.

EXAMPLES 1–9 AND COMPARATIVE EXAMPLES A–O

Effect of Armoblen® ACER 89002 (ACER) and Winter Oil (Oil) on Hydrogen Cyanamide (HC) Rest-Breaking Agent in Golden Delicious Apples In Examples 1–9, various combinations of Dormex™ (hydrogen cyanamide rest breaking agent) and Armoblen® ACER 89002 (activity promoting additive) in aqueous spray solutions were employed as rest-breaking agents in Golden Delicious apples. These tests were carried out in a region having a winter chill factor of less than 300 Richardson chill units.

The treatments of all the field trials in the examples have all been applied by motor driven piston pump equipment fitted with hand held spray lances. Operating pressure was kept at a constant two Bars.

Armoblen® ACER 89002 can be represented by the general formula:

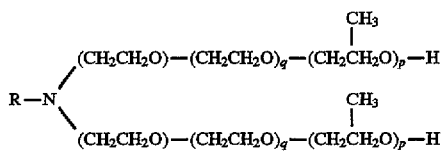

wherein p=12, q=4 and R is a hydrocarbon group derived from tallow fatty acid.

Comparative Example A is the control example where no rest-breaking agent was applied. Comparative Examples B–D demonstrate the effects of various amounts of hydrogen cyanamide alone. Comparative Examples E–G demonstrate the effects of various amounts of Armoblen® ACER 89002 alone. Comparative Examples H–I demonstrate the effect of various amounts of winter oil when used alone. Comparative Examples J–O demonstrate the effects of various combinations of winter oil and hydrogen cyanamide.

As far as timing of the applications is concerned, all materials were applied at the same time. The amounts of winter oil appear to be high relative to the amount of Armoblen® ACER 89002. However, the amounts of winter oil employed in the examples, namely 3.0–5.0%, are the amounts which are currently employed in practice.

Results

The following Table I gives the results obtained in these examples. All amounts are volume percent, based on the total volume of the aqueous solution.

The results for budbreak represent the absolute amount of budbreak (amount of budding per tree). The results for fruit set represent the number of fruit per flower cluster on the tree.

TABLE 1

| Example | HC | Oil | ACER | Bud Break | Fruit Set |
|---------|-----|-----|------|-----------|-----------|
| A | 0 | 0 | 0 | 16.34 | 2.39 |
| 1 | 1.0 | 0 | 0.1 | 17.03 | 1.21 |
| 2 | 2.0 | 0 | 0.1 | 26.28 | 1.33 |
| 3 | 4.0 | 0 | 0.1 | 25.92 | 0.80 |
| 4 | 1.0 | 0 | 0.5 | 19.91 | 2.04 |
| 5 | 2.0 | 0 | 0.5 | 19.38 | 1.59 |
| 6 | 4.0 | 0 | 0.5 | 26.80 | 1.34 |
| 7 | 1.0 | 0 | 1.0 | 22.00 | 1.47 |
| 8 | 2.0 | 0 | 1.0 | 17.24 | 1.11 |
| 9 | 4.0 | 0 | 1.0 | 20.04 | 1.09 |
| B | 1.0 | 0 | 0 | 19.56 | 1.13 |
| C | 2.0 | 0 | 0 | 22.38 | 1.15 |
| D | 4.0 | 0 | 0 | 27.53 | 1.13 |
| E | 0 | 0 | 0.1 | 15.11 | 1.65 |
| F | 0 | 0 | 0.5 | 21.40 | 2.34 |
| G | 0 | 0 | 1.0 | 13.06 | 1.83 |
| H | 0 | 3.0 | 0 | 14.75 | 1.60 |
| I | 0 | 5.0 | 0 | 18.87 | 1.65 |
| J | 1.0 | 3.0 | 0 | 13.61 | 1.40 |
| K | 2.0 | 3.0 | 0 | 14.19 | 1.16 |
| L | 4.0 | 3.0 | 0 | 12.78 | 0.97 |
| M | 1.0 | 5.0 | 0 | 16.54 | 1.18 |
| N | 2.0 | 5.0 | 0 | 14.47 | 0.77 |
| O | 4.0 | 5.0 | 0 | 9.56 | 1.49 |

These results demonstrate that the formulations of the present invention significantly improve the bud break while giving a fruit set of at least the same order as the prior art compositions.

EXAMPLES 10–17 AND COMPARATIVE EXAMPLES P–Y

Eight year old Golden Delicious trees grown at 1000 trees per hectare were treated with three liters of the following aqueous solutions per tree. The experiment had a completely randomized design and 5 repetitions per treatment were employed. These tests were carried out in a region with a somewhat harsher winter chilling of about 600 Richardson chilling units.

In Examples 10–13 and Comparative Examples P–Y, the rest-breaking agents were applied at the same time. In Examples 14–17, the rest-breaking agent KNO$_3$ was applied 10 days after the application of a solution of only the activity promoting additive ACER.

Comparative Example P was the control example. Comparative Examples Q and R were solutions of Armoblen® ACER-89002. Comparative Examples S–T were winter oil emulsions. Comparative Example U was a commercially used formulation of DNOC with winter oil emulsion. Comparative Examples V–Y were commercially used formulations of winter oil and hydrogen cyanamide. Examples 10–17 were Armoblen® ACER-89002 in various combinations with the milder rest-breaking agent potassium nitrate. The results are given in Table 2.

Results

For these examples budbreak is expressed as a percentage and fruit set is expressed as the number of fruit per tree.

TABLE 2

| Example | RBA | Amount RBA | Oil | ACER | Days Bloom Advanced | Budbreak (%) | Fruit Set |
|---------|-----|------------|-----|------|---------------------|--------------|-----------|
| P | — | 0 | 0 | 0 | — | 49 | 504.8 |
| Q | — | 0 | 0 | 1.0 | 5 | 49 | 399.4 |
| R | — | 0 | 0 | 2.0 | 10 | 52 | 525.2 |
| S | — | 0 | 2.0 | 0 | 10 | 61.5 | 283.8 |
| T | — | 0 | 3.0 | 0 | 16 | 49.5 | 323.8 |
| U | DNOC | 5.0 | 80.0 | 0 | 16 | 38 | 360.4 |
| V | HC | 0.5 | 2.0 | 0 | 22 | 59.5 | 531.6 |
| W | HC | 0.5 | 3.0 | 0 | 22 | 63 | 457.2 |
| X | HC | 0.75 | 2.0 | 0 | 27 | 77.5 | 669.8 |
| Y | HC | 0.75 | 3.0 | 0 | 27 | 67 | 491.8 |
| 10 | KNO$_3$ | 4.0 | 0 | 1.0 | 33 | 45.5 | 532 |
| 11 | KNO$_3$ | 4.0 | 0 | 2.0 | 36 | 47.5 | 547 |
| 12 | KNO$_3$ | 8.0 | 0 | 1.0 | 22 | 37.5 | 717.6 |
| 13 | KNO$_3$ | 8.0 | 0 | 2.0 | 36 | 58.5 | 1276.2 |
| 14 | KNO$_3$ | 4.0 | 0 | 1.0 | 5 | 44.5 | 401.4 |
| 15 | KNO$_3$ | 4.0 | 0 | 2.0 | 22 | 32.5 | 469 |
| 16 | KNO$_3$ | 8.0 | 0 | 1.0 | 16 | 40 | 387.6 |
| 17 | KNO$_3$ | 8.0 | 0 | 2.0 | 22 | 42 | 529.6 |

These results show that the compositions of the present invention advanced the time of bloom more than that of the compositions of hydrogen cyanamide/winter oil and were significantly better than the DNOC/oil. The activity promoting additive alone (ACER) seemed to delay the time of bloom relative to control trees.

thinned is expressed as both the grams and number of fruit thinned.

TABLE 3

| Example | KNO₃ | Oil | ACER | Days Before Full Bloom | Leaf Cover | Grams Fruit Thinned | No Fruit Thinned |
|---------|------|-----|------|------------------------|------------|---------------------|------------------|
| Z  | 0    | 0   | 0   | 1.66  | 3.67 | 51.5  | 17 |
| AA | 4.0  | 0   | 0   | 6.66  | 4.00 | 30.1  | 8  |
| BB | 8.0  | 0   | 0   | 5.00  | 3.00 | 49.7  | 12 |
| CC | 12.0 | 0   | 0   | 8.33  | 3.67 | 69.9  | 12 |
| DD | 4.0  | 2.0 | 0   | 3.33  | 3.33 | 45.5  | 9  |
| EE | 4.0  | 4.0 | 0   | 3.33  | 3.00 | 9.0   | 3  |
| FF | 4.0  | 6.0 | 0   | 1.66  | 2.00 | 0     | 0  |
| GG | 8.0  | 2.0 | 0   | 6.66  | 3.00 | 25.9  | 11 |
| HH | 8.0  | 4.0 | 0   | 5.00  | 3.00 | 22.6  | 6  |
| II | 8.0  | 6.0 | 0   | 5.66  | 2.67 | 51.6  | 15 |
| JJ | 12.0 | 2.0 | 0   | 5.00  | 3.33 | 49.7  | 13 |
| KK | 12.0 | 4.0 | 0   | 6.66  | 2.67 | 118.6 | 21 |
| LL | 12.0 | 6.0 | 0   | 6.66  | 4.00 | 29.6  | 4  |
| MM | *    | 0   | 0   | 18.33 | 4.00 | 66.2  | 8  |
| 18 | 4.0  | 0   | 0.5 | 3.33  | 2.67 | 12.2  | 3  |
| 19 | 4.0  | 0   | 1.0 | 8.33  | 4.00 | 77.2  | 19 |
| 20 | 4.0  | 0   | 2.0 | 6.66  | 3.67 | 149.5 | 41 |
| 21 | 8.0  | 0   | 0.5 | 1.66  | 2.57 | 43    | 18 |
| 22 | 8.0  | 0   | 1.0 | 5.00  | 3.00 | 88.2  | 18 |
| 23 | 8.0  | 0   | 2.0 | 6.66  | 3.33 | 44.6  | 12 |
| 24 | 12.0 | 0   | 0.5 | 3.33  | 2.67 | 31.1  | 7  |
| 25 | 12.0 | 0   | 1.0 | 3.33  | 3.00 | 0     | 0  |
| 26 | 12.0 | 0   | 2.0 | 6.66  | 3.00 | 43.5  | 10 |

*4.0% Hydrogen Cyanamide

The winter oil and winter oil and cyanamide gave the best results for budbreak. However, the effect of the milder, less toxic rest-breaking agents of the invention is apparent from these tests and shows positive results.

With respect to fruit set, the rest-breaking agents of the invention performed generally better than the harsher commercially applied rest breaking agents and, particularly in Example 13, an exceptional result was obtained.

EXAMPLES 18–26 AND COMPARATIVE EXAMPLES Z–MM

Five year old Golden Delicious trees planted in high density were treated with three liters of the following aqueous solutions per tree. The experiment had a completely randomized design and 3 repetitions per treatment were employed. These tests were carried out in a region with only mild winter chilling of less than 300 Richardson chilling units.

In Examples 18–26 and Comparative Examples Z–CC and MM, the rest-breaking agents were applied at the same time. In Examples DD–LL, the rest-breaking agent KNO₃ was applied 10 days later.

Comparative Example Z was the control example. Comparative Examples AA–CC were solutions of KNO₃. Comparative Examples DD–LL formulations of winter oil and KNO₃. Examples 18–26 were Armoblen® ACER-89002 in various combinations with KNO₃. Comparative Example MM was 4% hydrogen cyanamide. The results are given in Table 3.

Results

For these examples leaf cover is expressed as a rating of from 1–5 with 5 being the best and 1 being the worst. Fruit These results show that the relatively toxic hydrogen cyanamide gives the best results with respect to days before full bloom. However, a treatment of 1% ACER with 4% KNO₃ is shown to be equal in effect to a treatment with 6% winter oil and 12% KNO₃. Thus, the activity promoting additive of the present invention can be used in smaller quantities than the winter oil and allows a significant reduction in the amount of mild rest-breaking agent while increasing the level of rest-breaking activity.

The best results for leaf cover were obtained with the hydrogen cyanamide, 1% ACER plus 4% KNO₃ and 2% winter oil with 12% KNO₃ again demonstrating that the activity promoting additive of the present invention allows a reduction in the quantity of rest-breaking agent required to achieve a good result.

The best results for fruit set were obtained with the 12% KNO₃, the 1% and 2% ACER with 4% KNO₃ and the 4% winter oil with 12% KNO₃. Again a significant reduction in the amount of rest-breaking agent is made possible by the present invention.

EXAMPLES 27–30 AND COMPARATIVE EXAMPLES NN–QQ

Nine year old Golden Delicious trees grown at 1000 trees per hectare were treated with three liters of the following aqueous solutions per tree. The experiment had a completely randomized design and 5 repetitions per treatment were employed. These tests were carried out in a region with a somewhat harsher winter chilling of about 600 Richardson chilling units.

In all Examples, the rest-breaking agents were applied at the same time. Comparative Example NN was the control example. Comparative Example OO was DNOC/oil and Comparative Examples PP–QQ were ACER control examples. The results are given in Table 4.

Results

For these examples budbreak is expressed as a percentage and fruit set is expressed as the absolute number of fruit per tree.

TABLE 4

| Example | DNOC/Oil | KNO$_3$ | ACER | Days Bloom Advanced | Budbreak (%) | Fruit Set Number |
|---|---|---|---|---|---|---|
| NN | 0 | 0 | 0 | — | 49 | 450 |
| OO | 5.0 | 0 | 0 | 15.0 | 39 | 350 |
| PP | 0 | 0 | 1.0 | 4.0 | 49 | 400 |
| QQ | 0 | 0 | 2.0 | 10.0 | 52 | 550 |
| 27 | 0 | 4.0 | 1.0 | 33.G | 45 | 550 |
| 28 | 0 | 4.0 | 2.0 | 37.0 | 48 | 620 |
| 29 | 0 | 8.0 | 1.0 | 20.0 | 43 | 550 |
| 30 | 0 | 8.0 | 2.0 | 33.0 | 53 | 1200 |

These results show that the compositions of the present invention were better than the control and DNOC for budbreak and the time that bloom was advanced. Further, the fruit set was also improved by the treatments in accordance with the present invention and in Example 30 a dramatic improvement is observed.

EXAMPLES 31–39 AND COMPARATIVE EXAMPLES RR–VV

Six year old Golden Delicious trees planted in high density were treated with three liters of the following aqueous solutions per tree. The experiment had a completely randomized design and 3 repetitions per treatment were employed. These tests were carried out in a region with only mild winter chilling of less than 300 Richardson chilling units.

In all Examples the rest-breaking agents were applied at the same time. Comparative Example RR was the control example. Comparative Example VV was 2.04 hydrogen cyanamide. Comparative Examples SS–TT were ACER control examples. The results are given in Table 5.

Results

For these examples leaf cover is expressed as a rating of from 1–5 with 5 being the best and 1 being the worst. Fruit thinned is expressed as the number of fruit.

TABLE 5

| Example | HC | KNO$_3$ | ACER | Leafcover | Fruit Set Number |
|---|---|---|---|---|---|
| RR | 0 | 0 | 0 | 3.00 | 8 |
| SS | 0 | 4.0 | 0 | 3.67 | 6 |
| TT | 0 | 8.0 | 0 | 2.67 | 5 |
| UU | 0 | 12.0 | 0 | 3.33 | 11 |
| VV | 2.0 | 0 | 0 | 4.00 | 4 |
| 31 | 0 | 4.0 | 0.5 | 2.67 | 2 |
| 32 | 0 | 8.0 | 0.5 | 2.67 | 7 |
| 33 | 0 | 12.0 | 0.5 | 2.67 | 8 |
| 34 | 0 | 4.0 | 1.0 | 4.00 | 15 |
| 35 | 0 | 8.0 | 1.0 | 3.00 | 9 |
| 36 | 0 | 12.0 | 1.0 | 3.00 | 2 |
| 37 | 0 | 4.0 | 2.0 | 3.67 | 22 |
| 38 | 0 | 8.0 | 2.0 | 3.33 | 5 |
| 39 | 0 | 12..0 | 2.0 | 3.00 | 6 |

These tests show that the compositions of the present invention give an improvement over the control for leaf cover (an expression representing budbreak) and are as effective as the more toxic hydrogen cyanamide rest-breaking agent for leaf cover (budbreak). Again, the compositions of the present invention gave the best fruit set at 4% KNO$_3$.

The foregoing examples have been presented for purposes of illustration and description only and are not to be construed as limiting the scope of the invention in any manner. Accordingly, the scope of the invention is to be determined by the claims appended hereto.

What is claimed is:

1. A process for breaking the rest in deciduous fruit trees which comprises the step of applying to at least one deciduous fruit tree before blossom, 0.1 to 10% of at least one rest-breaking agent and a compound selected from alkoxylated amines represented by the following general formula:

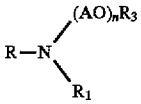

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

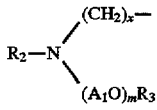

wherein m is an integer from 1–50, $A_1$ represents an alkylene group and when m>1, each $A_1$ may be the same or different alkylene groups, x is an integer from 1–6, and $R_2$ is independently selected from the same groups as R, $R_3$ is selected from hydrogen, straight or branched chain alkyl and alkenyl groups having from 1–8 carbon atoms and aryl groups having up to 8 carbon atoms; and $R_1$ is selected from hydrogen, straight or branched chain alkyl and alkenyl groups having 1–22 carbon atoms, or a group represented by the formula:

wherein n' is an integer from 1 to 50 and $A_2$ represents an alkylene group and when n'>1 each $A_2$ may be the same or different alkylene groups; and alkoxylated quaternary ammonium compounds represented by the following general formula:

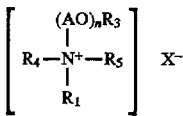

wherein n, A, $R_1$ and $R_3$ are as defined above, X is an anion, $R_5$ is selected from hydrogen, straight or branched chain alkyl or alkenyl groups having 1 to 4 carbon atoms, and benzyl or $R_5X^-$ is carboxymethyl and/or oxygen; $R_4$ is selected from straight or branched chain alkyl and alkenyl groups having 8–22 carbon atoms and groups represented by the formula:

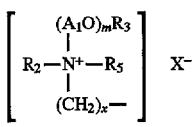

wherein A1, m, $R_2$, $R_3$, $R_5$, X, and x are as defined above; with the proviso that at most 6 nitrogen atoms are present in said compound; to enhance the rest-breaking of the deciduous fruit tree.

2. The process of claim 1 wherein said rest-breaking agent is applied in the form of an aqueous solution having a concentration of from 0.2 to 5.0% of said compound and from 0.5–30% of said rest-breaking agent.

3. The process of claim 2 wherein said compound has a molecular weight of less than 8000 grams/mole.

4. The process of claim 3 wherein said compound is an alkoxylated quaternary ammonium compound represented by the general formula:

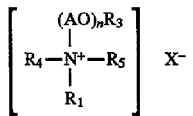

wherein n is an integer from 1 to 50, $X^-$ is an anion, A represents an alkylene group and when n>1, each A may be the same or different alkylene groups, $R_5$ is selected from hydrogen, straight or branched chain alkyl and alkenyl groups having 1–4 carbon atoms, and benzyl, or $R_5X^-$ is carboxymethyl, and/or oxygen; $R_4$ is selected from straight or branched chain alkyl or alkenyl groups having 8 to 22 carbon atoms or a group represented by the formula:

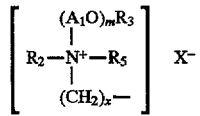

wherein m is an integer from 1 to 50, $X^-$ is an anion, $R_5$ is as defined above, $A_1$ represents an alkylene group and when M>1, each $A_1$ may be the same or different alkylene groups, x is an integer from 1 to 6, $R_2$ is selected from straight or branched chain alkyl or alkenyl groups having 8–22 carbon atoms; and $R_1$ is selected from hydrogen, straight or branched chain alkyl or alkenyl groups having 1 to 22 carbon atoms, or a group represented by the formula:

wherein n' is an integer from 1 to 50 and $A_2$ represents an alkylene group; when n'>1 each $A_2$ may be the same or different alkylene groups, and $R_3$ is selected from hydrogen, straight or branched chain alkyl or alkenyl groups having 1 to 8 carbon atoms and aryl groups having up to 8 carbon atoms.

5. The process of claim 3 wherein said compound is an alkoxylated amine represented by the following general formula:

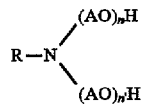

wherein n and n' are integers from 1 to 50, A represents an alkylene group and when n or n' are greater than 1, each A may be the same or different alkylene groups, and R is selected from straight or branched chain alkyl or alkenyl groups having 8 to 22 carbon atoms.

6. The process of claim 5 wherein n>1 and A includes both ethoxy groups and propoxy groups.

7. The process of claim 3 wherein said compound is an alkoxylated amine represented by the following general formula:

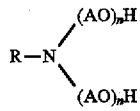

wherein n and n' are integers from 1 to 50, A represents an alkylene group and when n or n' are greater than 1, each A may be the same or different alkylene groups, R is a group represented by the formula:

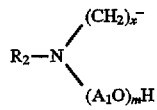

wherein m is an integer from 1 to 50, $A_1$ represents an alkylene group and when m>1, each $A_1$ may be the same or different alkylene groups; x is an integer from 1 to 6, and $R_2$ is selected from straight or branched chain alkyl or alkenyl groups having 8–22 carbon atoms.

8. The process of claim 3 wherein R is selected from alkyl groups having 12–22 carbon atoms.

9. The process of claim 3 wherein said compound is an amine oxide represented by the following general formula:

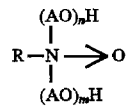

wherein R, A, n and m are as defined in claim 1.

10. A composition which comprises an effective amount of at least one agent for breaking the rest in deciduous fruit trees and 0.1–10% of at least one compound selected from alkoxylated amines represented by the following general formula which is effective to enhance the activity of said rest breaking agent:

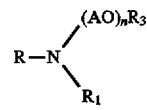

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

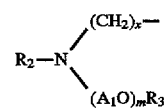

wherein m is an integer from 1–50, $A_1$ represents an alkylene group and when m>1, each $A_1$ may be the same or different alkylene groups, x is an integer from 1–6, and $R_2$ is independently selected from the same groups as R, $R_3$ is selected from hydrogen, straight or branched chain alkyl and alkenyl groups having from 1 to 8 carbon atoms and aryl groups having up to 8 carbon atoms; and $R_1$ is selected from hydrogen, straight or branched chain alkyl and alkenyl groups having 1–22 carbon atoms, or a group represented by the formula:

$$(A_2O)_{n'}R_3$$

wherein n' is an integer from 1 to 50 and $A_2$ represents an alkylene group and when n'>1 each $A_2$ may be the same or different alkylene groups; and alkoxylated quaternary ammonium compounds represented by the following general formula:

$$\left[ \begin{array}{c} (AO)_nR_3 \\ | \\ R_4-N^+-R_5 \\ | \\ R_1 \end{array} \right] X^-$$

wherein n, A, $R_1$ and $R_3$ are as defined above, X is an anion, $R_5$ is selected from hydrogen, straight or branched chain alkyl or alkenyl groups having 1 to 4 carbon atoms, and benzyl or $R_5X^-$ is carboxymethyl and/or oxygen; $R_4$ is selected from straight or branched chain alkyl and alkenyl groups having 8–22 carbon atoms and groups represented by the formula:

$$\left[ \begin{array}{c} (A_1O)_mR_3 \\ | \\ R_2-N^+-R_5 \\ | \\ (CH_2)_x- \end{array} \right] X^-$$

wherein $A_1$, m, $R_2$, $R_3$, $R_5$, X, and x are as defined above; with the proviso that at most 6 nitrogen atoms are present in said compound.

11. A composition in accordance with claim 10 wherein said compound has a molecular weight of less than 8000 grams/mole and is an alkoxylated amine represented by the following general formula:

$$R-N \begin{array}{c} (AO)_nH \\ \diagdown \\ (AO)_{n'}H \end{array}$$

wherein n and n' are integers from 1 to 50, A represents an alkylene group and when n or n' are greater than 1, each A may be the same or different alkylene groups, and R is selected from straight or branched chain alkyl or alkenyl groups having 8 to 22 carbon atoms.

* * * * *